United States Patent [19]

Brand et al.

[11] 3,968,244

[45] July 6, 1976

[54] CHEMOSTERILANT AND LARVICIDAL IMIDOTHIOCARBONATES

[75] Inventors: William Wayne Brand, Hopewell; Michael Stanley Schrider, South Bound Brook, both of N.J.

[73] Assignee: American Cyanamid Company, Stamford, Conn.

[22] Filed: Jan. 14, 1975

[21] Appl. No.: 540,935

Related U.S. Application Data

[62] Division of Ser. No. 410,842, Oct. 28, 1973, Pat. No. 3,892,761.

[52] U.S. Cl. ............................... 424/330; 424/263
[51] Int. Cl.² ...................... A01N 9/20; A01N 9/22

[58] Field of Search.................... 424/263, 301, 330

[56] References Cited

UNITED STATES PATENTS 3,832,351   8/1974   Tanaka et al. ................ 260/294.8 E

OTHER PUBLICATIONS

Insect Chemosterilants, Borkovec (1966), pp. 61–63.

*Primary Examiner*—Jerome D. Goldberg
*Assistant Examiner*—Allen J. Robinson
*Attorney, Agent, or Firm*—Denis A. Polyn

[57] ABSTRACT

This disclosure describes esters of dithioimidocarbonic acid having chemosterilant and larvicidal activity.

10 Claims, No Drawings

CHEMOSTERILANT AND LARVICIDAL IMIDOTHIOCARBONATES

CROSS REFERENCE TO RELATED APPLICATION

This application is a division of our copending application Ser. No. 410,842, filed Oct. 28, 1973, now U.S. Pat. No. 3,892,761.

BRIEF SUMMARY OF THE INVENTION

This invention relates to new organic compounds and, more particularly, is concerned with novel esters of dithioimidocarbonic acid and methods of preparing these compounds. The novel compounds of the present invention may be represented by the following general formula:

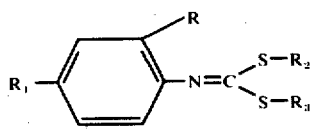

wherein R is chloro or methyl, $R_1$ is chloro or methyl, and $R_2$ and $R_3$ are each selected from the group consisting of lower alkyl, lower alkylthiomethyl, allyl, 2-chloroallyl, 2-methylallyl, propargyl, 4-pyridylmethyl and benzyl, with the proviso that $R_2$ and $R_3$ cannot both be lower alkyl. Suitable lower alkyl groups comtemplated by the present invention are those having up to six carbon atoms such as methyl, ethyl, n-propyl, isopropyl, n-butyl, isobutyl, 2-pentyl, 3-pentyl, 2-hexyl, isohexyl, etc. A preferred class of compounds within the above general formula are those wherein R is methyl and $R_1$ is chloro.

This invention further relates to the use of these esters of dithioimidocarbonic acid in controlling acarina. More particularly, it relates to controlling acarina by suppressing the fecundity thereof with effective amounts of these compounds. Further, it relates to the control of acarina by applying the compounds to adult acarina, or to the habitat or dietary media (such as foliage or vegetation, manure and the like) of acarina in an amount sufficient to suppress the fecundity thereof. It also relates to controlling acarina by applying a larvicidally effective amount of these compounds to the larvae, larval habitat, or dietary media of the larvae of acarina.

This invention also relates to a method for controlling Ixodidae by suppressing the fecundity thereof. It further relates to controlling Ixodidae by applying a larvicidally effective amount of these esters of dithioimidocarbonic acid to the larvae, larval habitat, or dietary media of the larvae of Ixodidae. Still more particularly, this invention relates to a method for controlling ixodid ticks by applying a fecundity-suppressing amount of these esters of dithioimidocarbonic acid to adult ixodid ticks, or to the habitat or dietary media of ixodid ticks.

This invention further relates to chemosterilant and larvicidal compositions containing these esters of dithioimidocarbonic acid.

DETAILED DESCRIPTION OF THE INVENTION

The novel compounds of the present invention are preferably prepared by reacting an appropriate dithiocarbamate ester with an appropriate reactive halide in accordance with the following reaction scheme:

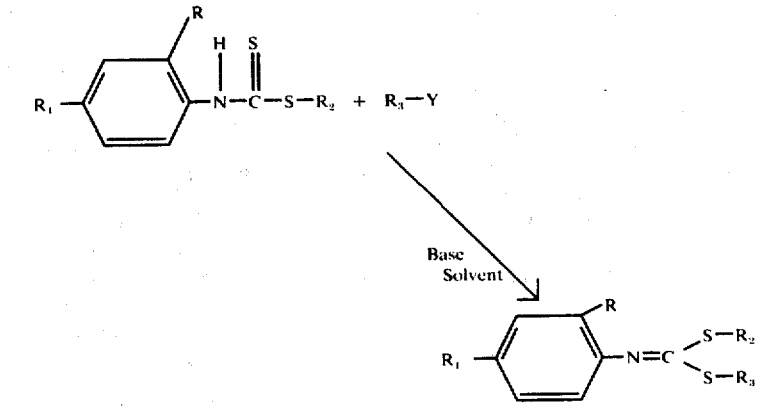

wherein R, $R_1$, $R_2$, and $R_3$ are as previously defined and Y represents a suitable leaving group such as a reactive halo group or alkyl or aryl sulfonate. The reaction is generally carried out in the presence of (1) a base such as an alkali metal hydroxide, carbonate or bicarbonate, a tertiary amine or other weak base and (2) an organic solvent such as methyl alcohol or dimethylformamide. This reaction is carried out at a relatively low temperature, for example between about −10°C. and 50°C., and preferably at about 0°C. to 25°C. The reaction product is isolated by pouring the reaction mixture into water and extracting the aqueous solution with a water-insoluble solvent such as diethyl ether, chloroform, and the like. The product is recovered from the extract by evaporation of the excess solvent and purified by distillation, dry-column chromatography, or recrystallization depending on the particular product being prepared.

The dithiocarbamate ester can be prepared by reacting an appropriate alkali metal or ammonium dithiocarbamate salt with an appropriate reactive halide as reported by Reid [Organic Chemistry of Bivalent Sulfur, Chemical Publishing Co., Inc., New York, Vol. IV (1962) page 235] and as shown below:

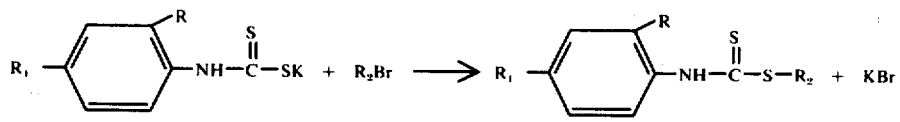

The dithiocarbamate salt can be prepared by reacting the appropriate amine with carbon disulfide and base, or it can be synthesized from the appropriately substituted isothiocyanate by reaction with an alkali metal hydrosulfide in a suitable solvent. Alternatively, the intermediate dithiocarbamate ester can be prepared by reaction of an appropriate isothiocyanate with an appropriate thiol.

The compounds of the present invention can also be prepared from the corresponding isocyanide dichlorides by the method described by E. Kuhle in Angew. Chem. Internat. Edit., 8, 20 (1969).

Typical compounds of the present invention which may be prepared by the above methods are, for example, n-pentyl (ethylthio)methyl (2,4-dichlorophenyl)-dithioimidocarbonate, benzyl (isopropylthio)methyl (2,4-dichlorophenyl)dithioimidocarbonate, allyl (n-propylthio)methyl (2,4-dichlorophenyl)dithioimidocarbonate, allyl 2-propynyl (2,4-dichlorophenyl)dithioimidocarbonate, 2-propynyl (sec-butylthio)methyl (2,4-xylyl)dithioimidocarbonate, 2-methylallyl (n-butylthio)methyl (2,4-xylyl)dithioimidocarbonate, isopropyl benzyl (2,4-xylyl)dithioimidocarbonate, n-propyl (amylthio)methyl (2-chloro-p-tolyl)dithioimidocarbonate, isobutyl (n-hexylthio)methyl (2-chloro-p-tolyl)dithioimidocarbonate, and sec-butyl 2-chloroallyl (2-chloro-p-tolyl)dithioimidocarbonate.

The novel compounds of the present invention may be used to control infestations of acarina on mammals and birds, generally, and are particularly useful in controlling tick infestations of livestock, such as cattle, swine, sheep and goats, of domestic pets, such as dogs and cats, of rabbits, of poultry such as chickens, turkeys, geese, and the like, of fur bearing animals such as mink, foxes, chinchillas, and the like. When the compounds of this invention are utilized as control agents for acarina, such compounds may be brought into contact in effective amounts with the adult pest, ova or larva of said pests, or they may be applied to the habitat, breeding grounds and/or dietary media of said pest or larvae, that is, organic matter, living or dead which forms their food. The application is preferably made at a dosage concentration which is sublethal for adult acarina, but which level provides ultimate control of said acarina through ovicidal or larvicidal activity or by suppression of fecundity, inhibition of metamorphosis, juvenile hormone effect or chemosterilization of said pests. However, in some cases adult pests may receive a lethal dosage particularly with high concentration levels.

In practice, the active compounds are generally formulated with conventional solid or liquid adjuvants or formulation aids and applied by conventional means. They may be formulated as dusts, dust concentrates, wettable powders, emulsifiable concentrates or the like. They may also be incorporated in baits upon which acarina feed. Dusts or dust concentrates, can be prepared by grinding together an inert solid diluent such as attapulgite, kaolin, walnut shell flour, diatomaceous earth, ground corn cob grits, or ground cocoanut shell, and the active ingredient, where such active ingredient is in solid form. Where the active ingredient is liquid, it may be sprayed on the carrier and thoroughly mixed with it or it may be dissolved in a solvent such as acetone or xylene, and the solution sprayed on the solid carrier. Dusts usually contain from about 1% to 15% by weight of active ingredient, whereas concentrates may contain from about 16% to about 85% by weight of the active material. Wettable powders are prepared in the same fashion as dust concentrates, excepting that about 5% to 10% by weight of a surfactant is also added.

The compounds of the present invention may also be prepared as emulsifiable concentrates by dissolving or dispersing about 10% to 75% by weight of the active compound in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application. Wettable powders and emulsifiable concentrates are particularly useful since they can be diluted with water and applied as dilute liquid sprays to an infested area or animal for which protection is sought or they may be sprayed on or applied topically to animals which are to be protected from attack. In the latter situation the dilute formulation may be used as dips as well as sprays. Field application of these formulations may be made by conventional equipment, such as power dusters, boom and hand sprayers, spray dusters, spray races and the like.

The dithioimidocarbonate esters may be particularly used to control Ixodidae populations by application thereof to Argasid or Ixodid adult female ticks as Boophilus, Amblyomma, Anocentor, Dermacentor, Ixodes, Haemaphysalis, Hyalomma, Rhipicentor, Margarpus, Rhipicephalus, Argas, Otobius and Ornithodors whereby fecundity is suppressed, i.e., their egg production is inhibited, or if laid, the embryogenesis of the egg is prevented.

The dosage employed will depend upon the particular composition to be used, the particular kind or kinds of acarina to be controlled, the degree of infestation and the particular result desired. These factors are those ordinarily encountered in animal husbandry to control and/or prevent infestations of ectoparasites; these factors are well known to the practitioners of the art. In general larger doses are required to control an already existing infestation. In the practice of this invention, we have found that the fecundity of acarina can be suppressed by thoroughly spraying an infested animal with a dilute aqueous dispersion containing from 0.001% active ingredient w/w to 0.2% active ingredient w/w; each animal is thoroughly sprayed with from 1.5 to 10 liters of solution. Control of the larval stages of acarina on animals can be obtained with the ester of dithioimidocarbonic acid in dilute formulations containing from about 0.001% w/w to 0.20% w/w of the active ingredient, preferably 0.001% w/w to 0.10% w/w of the active ingredient. Control of infested areas can be effected by the application of from about 1/8 pound to 15 pounds of active ingredient per acre. Preferably, the rate of application ranges from about 1/8 pound to 10 pounds of active ingredient per acre.

The preparation and the effectiveness of the novel compounds of the present invention are further demonstrated in the following examples which are not to be taken as being limitative of the present invention. Unless otherwise indicated all parts and percentages employed herein are by weight.

EXAMPLE 1

Preparation of di-2-propynyl (4-chloro-o-tolyl)dithioimidocarbonate

A solution of 52.4 g. (0.44 mole) of propargyl bromide in 400 ml. of methanol is cooled to 0°–5°C. with an ice bath. To this is added portionwise during 20 minutes, 63.9 g. (0.2 mole) of triethylammonium (4-chloro-o-tolyl)dithiocarbamate followed by the dropwise addition during 20 minutes of a solution of 28 ml. (0.2 mole) of triethylamine in 50 ml. of methanol. Stirring is continued for 2 days during which the reaction mixture is warmed to room temperature. The reaction mixture is then filtered, and the solids are washed with methanol giving 9.6 g. (16.3% yield) of the product as a white solid. The filtrate is diluted to 3 liters with diethyl ether and the precipitated triethylamine hydrobromide (63.9 g., 88%) is filtered off and washed with diethyl ether. The filtrate is then concentrated in vacuo, and the residual brown semisolid is stirred with 600 ml. of hot hexane, filtered hot to remove triethylamine hydrobromide, and allowed to cool. The resulting solid weighs 21.9 g. (37.3% yield), giving a total yield of 31.5 g. (53.6%) of product. Recrystallization from hexane-pentane gives white needles, m.p. 74.5–75.5°C.

EXAMPLE 2

Preparation of diallyl (4-chloro-o-tolyl)dithioimidocarbonate

To 18.3 g. (0.067 m.) of allyl (4-chloro-o-tolyl)dithiocarbamate and 2.74 g. (0.067 m.) of sodium hydroxide beads in 100 ml. of dimethylformamide is added 8.1 g. (0.067 m.) of allyl bromide, with occasional cooling to keep the temperature at 25°C. After the beads are completely dissolved the mixture is poured into 800 ml. of water and extracted with 100 ml. of chloroform. The aqueous layer is extracted again with 100 ml. of chloroform, and the chloroform extracts are combined and washed with water. On drying and concentration, a yellow liquid is obtained which is passed through a dry-column using 5% methylene chloride in hexane, and 9.8 g. (49% theory) of a pale yellow liquid is obtained. Nuclear magnetic resonance and infrared spectra are in agreement with the assigned structure.

EXAMPLE 3

Preparation of allyl (methylthio)methyl (2,4-xylyl)dithioimidocarbonate

Chloromethyl methyl sulfide is allowed to react with allyl (2,4-xylyl)dithiocarbamate following the procedure of Example 2. There resulted a 77% yield of yellow oil, the nuclear magnetic resonance and infrared spectra of which are consistent with the desired product.

EXAMPLE 4

Preparation of ethyl 2-propynyl (4-chloro-o-tolyl)dithioimidocarbonate

Ethyl (4-chloro-o-tolyl)dithiocarbamate is allowed to react with propargyl bromide following the procedure of Example 2. There results a 47.5% yield of product having nuclear magnetic resonance and infrared spectra, and elemental analysis in agreement with the assigned structure.

EXAMPLE 5

Preparation of allyl (methylthio)methyl (4-chloro-o-tolyl)dithiomidocarbonate

Allyl (4-chloro-o-tolyl)dithiocarbamate is allowed to react with chloromethyl methyl sulfide following the procedure of Example 2. There results a 46.5% yield of product having nuclear magnetic resonance and infrared spectra, and elemental analysis in agreement with the assigned structure.

EXAMPLE 6

Preparation of allyl tert-butyl (4-chloro-o-tolyl)dithioimidocarbonate

To 9.2 g. (0.05 m.) of (4-chloro-o-tolyl) isothiocyanate and 2.1 g. (0.05 m.) of sodium hydroxide beads in 50 ml. of dimethylformamide, is added 4.5 g. (0.05 m.) of t-butyl mercaptan. Occasional cooling is necessary to keep the temperature at 25°C. After one hour, 6.1 g. (0.05 m.) of allyl bromide is added, dropwise, keeping the temperature at 25°C. After an additional hour the solution is poured into 500 ml. of water and 100 ml. of chloroform and the chloroform layer is separated. The aqueous phase is extracted with another 100 ml. of chloroform, and the chloroform layers are combined and washed with water. On drying and concentration, an orange liquid is obtained which is passed through a dry-column using 5% methylene chloride in hexane as the eluent to obtain 10.2 g. (64% of theory) of a pale yellow liquid. The infrared and nuclear magnetic resonance spectra are in agreement with the assigned structure.

EXAMPLE 7

Preparation of allyl ethyl (4-chloro-o-tolyl)dithioimidocarbonate

Ethyl (4-chloro-o-tolyl)dithiocarbamate is allowed to react with allyl bromide following the procedure of Example 2. There results an 85.6% yield of a liquid, b.p. 132.5°–134.5°C., 0.1 mm., having infrared and nuclear magnetic resonance spectra, and elemental analysis in agreement with the assigned structure.

EXAMPLE 8

Preparation of ethyl 2-methylallyl (4-chloro-o-tolyl)dithioimidocarbonate

Ethyl (4-chloro-o-tolyl)dithiocarbamate is allowed to react with methallyl chloride following the procedure of Example 2. There results a 55% yield of product having infrared and nuclear magnetic resonance spectra in agreement with the assigned structure.

EXAMPLE 9

Preparation of bis(2-chloroallyl) (4-chloro-o-tolyl)dithioimidocarbonate

To a stirred mixture of 16.0 g. (0.05 mole) of triethylammonium (4-chloro-o-tolyl)dithiocarbamate, 5.0 g. (0.05 mole) of triethylamine, and 75 ml. of dimethylformamide is added dropwise 11.1 g. (0.1 mole) of 2,3-dichloro-1-propene. The resulting mixture is stirred for several hours, poured into water, and extracted with ether. The ether extract is washed with water, dried and concentrated. The residue is purified on a silica gel dry column with 5% methylene chloride in hexane as eluent, giving 7.1 g. (38.5% yield) of a pale yellow liquid. Infrared and nuclear magnetic resonance spectra are in agreement with the assigned structure.

EXAMPLE 10

Preparation of allyl 2-propynyl (4-chloro-o-tolyl)dithioimidocarbonate

Propargyl bromide was allowed to react with allyl (4-chloro-o-tolyl)dithiocarbamate following the procedure of Example 2. There resulted a 14% yield of the product after purification.

EXAMPLE 11

Preparation of di-2-propynyl (2,4-xylyl)dithioimidocarbonate

A solution of 13.1 g. (0.11 mole) of propargyl bromide in 100 ml. of methanol is cooled to 0°–5°C. with an ice bath. To this is added portionwise 14.9 g. (0.05 mole) of triethylammonium (2,4xylyl)dithiocarbamate. The reaction mixture is stirred at 0°–5°C. for 15 minutes after which a solution of 7 ml. (0.05 mole) of triethylamine in 10 ml. of methanol is added dropwise. After 30 minutes, the ice bath is removed, and the reaction mixture is stirred overnight. The reaction mixture is then concentrated, and the residue is partitioned between water and diethyl ether. The ether solution is washed with water, 6M HCl, water, and finally saturated NaHCO$_3$. The ether solution is then dried and the solvent distilled out leaving 11.31 g. of a yellow oil. This is partially purified by chromatography on a silica gel dry column with 1:3 methylene chloride/hexane. The fraction containing product is taken up in diethyl ether, treated with charcoal and anhydrous magnesium sulfate, filtered, and concentrated giving 0.5 g. (3.7% yield) of a brown-yellow solid, m.p. 38°–42°C., having infrared and nuclear magnetic resonance spectra consistent with the desired product.

EXAMPLE 12

Preparation of allyl hexyl (4-chloro-o-tolyl)dithioimidocarbonate

To 16.0 g. of allyl (4-chloro-o-tolyl)dithiocarbamate and 2.4 g. of sodium hydroxide beads stirred with 100 ml. of dimethylformamide is added 9.65 g. of n-hexylbromide, dropwise while keeping the temperature below 30°C. After stirring for about one hour the reaction mixture is poured into one liter of water. Following the procedure of Example 2, an orange liquid is separated and distilled; the fraction boiling between 174.5°–177°C. at 0.050 mm. pressure is collected. The distillate is then purified on a dry column of silica gel with a mixture of 5% methylene dichloride – 95% hexane to separate an isothiocyanate impurity. A yellow band is then eluted from the column and concentrated to obtain 9.8 g. of a pale yellow liquid which has a nuclear magnetic resonance spectrum in agreement with the assigned structure.

EXAMPLE 13

Preparation of ethyl 4-pyridylmethyl (4-chloro-o-tolyl)dithioimidocarbonate

To 16.4 g. of ethyl (4-chloro-o-tolyl)dithiocarbamate and 9.84 g. of 4-picolyl chloride hydrochloride in 100 ml. of dimethylformamide is added 12.2 g. of triethylamine, dropwise, while keeping the temperature at 25°C. The reaction mixture is then stirred at room temperature for about one hour, poured into water and extracted with two 250-ml. portions of chloroform. The combined chloroform extract is washed with water, dried and concentrated to a dark reddish liquid. The liquid is purified on a dry column of silica gel with a mixture of 66.6% methylene dichloride – 33.3% methyl ethyl ketone. The separation of the various fractions is determined by the presence of ultraviolet absorption. A major fraction preceding a yellow band is concentrated to obtain 7.4 g. of a yellow-orange liquid which has infrared and nuclear magnetic resonance spectra which corresponded to the assigned structure.

EXAMPLE 14

Preparation of dibenzyl (4-chloro-o-tolyl)dithioimidocarbonate

To 20.0 g. of benzyl (4-chloro-o-tolyl)dithiocarbamate dissolved in 100 ml. of dimethylformamide is added 2.38 g. of sodium hydroxide beads. To this solution 10.1 g. of benzyl bromide is then added dropwise, keeping the temperature between 25°–30°C. After stirring for about 1 hour at room temperature the reaction mixture is poured into 1 liter of water and extracted with 2 × 250 ml. of chloroform. The chloroform extract is washed with one liter of water, dried and concentrated to obtain 23.4 g. of a yellow-orange liquid. This material is purified on a dry column of silica gel using a solution of 10% methylene dichloride – 90% hexane. A fraction immediately following a bright yellow band is separated and concentrated to obtain 5.0 g. of a white solid m.p. 84°–86°C.

EXAMPLE 15

Preparation of bis(2-chloroallyl) (2,4-dichlorophenyl)dithioimidocarbonate

The procedure of Example 9 is used except that triethylammonium-(2,4-dichlorophenyl)dithiocarbamate is used instead of triethylammonium-(4-chloro-o-tolyl)dithiocarbamate. The product obtained has infrared and nuclear magnetic resonance spectra in agreement with the assigned structure.

EXAMPLE 16

Preparation of benzyl ethyl (4-chloro-o-tolyl)dithioimidocarbonate

To 7.37 grams (0.03 mole) of ethyl (4-chloro-o-tolyl)dithiocarbamate in 75 ml. of t-butanol at 20°C. is added, gradually, 3.36 grams (0.03 mole) of potassium t-butoxide. To this mixture is gradually added 5.13 grams (0.03 mole) of benzyl bromide while allowing the temperature to rise to about 31°C. The mixture is stirred at room temperature for about 2.5 hours, filtered, and the filter cake is washed with diethyl ether.

The filtrate is filtered a second time and evaporated to dryness to obtain an oil. The oil is diluted with 150 ml. of pentane and allowed to stand overnight. The diluted solution is filtered and the filtrate is evaporated to dryness to obtain 9.88 grams of a viscous oil. The viscous oil is distilled in vacuo to obtain a fraction boiling between 173°C. to 176°C. at 0.025 Torr.

EXAMPLE 17

Preparation of ethyl (methylthio)methyl (4-chloro-o-tolyl)dithioimidocarbonate

To 7.37 grams (0.03 mole) of ethyl (4-chloro-o-tolyl)dithiocarbamate in 75 ml. of t-butanol is added 3.36 grams (0.03 mole) of potassium t-butoxide and then 3.0 grams (0.031 mole) of chloromethyl methyl thioether. Upon completion of addition of the latter, the mixture is stirred at room temperature for 3.5 hours, 75 ml. of pentane is added thereto, and the reaction mixture is filtered. The filter cake is washed with pentane, and the combined filtrate and washings are concentrated in vacuo to obtain an amber-colored oil. Distillation of the oil in vacuo gives a pale yellow oil boiling at 144°C. to 148°C. at 0.04 mm to 0.05 mm. pressure.

EXAMPLE 18

Preparation of di-2-propynyl (2-chloro-p-tolyl)dithioimidocarbonate

Propargyl bromide is allowed to react with 2-propynyl (2-chloro-p-tolyl)dithiocarbamate following the procedure of Example 2. The resulting product is in agreement with the assigned structure.

EXAMPLE 19

Preparation of allyl 2-propynyl (2-chloro-p-tolyl)dithioimidocarbonate

Propargyl bromide is allowed to react with allyl (2-chloro-p-tolyl)-dithiocarbamate following the procedure of Example 2. The resulting product is in agreement with the assigned structure.

EXAMPLES 20 – 36

Suppression of Fecundity and Chemosterilant Effect in Ixodidae

The efficacy of the compounds of the present invention for suppression of fecundity in ticks is demonstrated in the following tests wherein engorged adult female *Boophilus microplus* ticks which have dropped from cattle are collected and used for testing.

The compound to be tested is dissolved in a 35% acetone/65% water mixture in sufficient amount to provide 500 ppm., 1,000 ppm. and 2,000 ppm. of compound in the test solution. Ten ticks per treatment are used and they are immersed in test solution for three to five minutes, then removed and placed in dishes and held in incubators for two to three weeks 28°C. Counts of ticks laying eggs are then made and recorded. Eggs which were laid are placed in containers and kept for one month to observe hatching and to determine chemosterilant effect. For each test, 10 non-resistant ticks as well as 10 ethion-resistant and 10 dioxathion-resistant ticks are used since the latter two are among the most difficult of their kind to control. Results of these tests are given in Tables I and II below. The rating system used for each tick is as follows:

Rating System

| Result | Score |
|---|---|
| No oviposition | 4 |
| Partial oviposition, no hatch | 3 |
| Total oviposition, no hatch | 2 |
| Partial oviposition, viable eggs | 1 |
| Normal oviposition and hatch | 0 |

The rating system is based on the summation of scores from all ticks regardless of the dose rate or strain of ticks tested. Using this rating system the best score possible would be 360, or 90 (the total number of ticks used) × 4 (the highest score). The efficacy is reported as percent of the best possible score.

TABLE I

Chemosterilant Efficacy of Dithiomidocarbonates

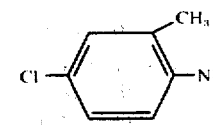

| Ex. No. | $R_2$ | $R_3$ | Efficacy % |
|---|---|---|---|
| 20 | —CH$_2$C≡CH | —CH$_2$C≡CH | 95 |
| 21 | —CH$_2$CH$_3$ | —CH$_2$S—CH$_3$ | 20 |
| 22 | —CH$_2$CH=CH$_2$ | —CH$_2$S—CH$_3$ | 75 |
| 23 | —CH$_2$CH=CH$_2$ | —CH$_2$CH=CH$_2$ | 79 |
| 24 | —CH$_2$C(Cl)=CH$_2$ | —CH$_2$C(Cl)=CH$_2$ | 63 |
| 25 | —CH$_2$C≡CH | —CH$_2$CH=CH$_2$ | 69 |
| 26 | —CH$_2$C≡CH | —CH$_2$CH$_3$ | 83 |
| 27 | —CH$_2$CH=CH$_2$ | —C(CH$_3$)$_3$ | 73 |
| 28 | —CH$_2$CH=CH$_2$ | —CH$_2$CH$_3$ | 69 |
| 29 | —CH$_2$C(CH$_3$)=CH$_2$ | —CH$_2$CH$_3$ | 66 |
| 30 | —CH$_2$—C$_6$H$_5$ | —CH$_2$—C$_6$H$_5$ | 53 |
| 31 | —CH$_2$CH=CH$_2$ | —(CH$_2$)$_5$CH$_3$ | 23 |
| 32 | —CH$_2$—(pyridyl) | —CH$_2$CH$_3$ | 62 |
| 33 | —CH$_2$—C$_6$H$_5$ | —CH$_2$CH$_3$ | 58 |

TABLE II

Chemosterilant Efficacy of Dithioimidocarbonates structure

| Ex. No. | R | $R_1$ | $R_2$ | $R_3$ | Efficacy (%) |
|---|---|---|---|---|---|
| 34 | —$CH_3$ | —$CH_3$ | —$CH_2C\equiv CH$ | —$CH_2C\equiv CH$ | 39 |
| 35 | —$CH_3$ | —$CH_3$ | —$CH_2S$—$CH_3$ | —$CH_2CH=CH_2$ | 82 |
| 36 | —Cl | —Cl | $\underset{Cl}{-CH_2\overset{|}{C}=CH_2}$ | $\underset{Cl}{-CH_2\overset{|}{C}=CH_2}$ | 22 |

EXAMPLES 37-50

Larvicidal Activity

The effective control of acarina larvae is demonstrated in the following tests with larvae of *Boophilus microplus*, a one-host tick which remains on a single host through its three life stages, i.e., larva, nymph and adult. In these tests, a 10% acetone/90% water mixture contains from 1.0 to 100 ppm. of test compound. Twenty larvae are enclosed in a pipet sealed at one end with a gauze material and solution containing the test compound is then drawn through the pipet with a vacuum hose simulating a spray system. The wet ticks are then held for 48 hours at room temperature and 80% relative humidity and mortality is determined. The rating system used is as follows:

Rating System

| Mortality | Concentration | Rating |
|---|---|---|
| >50% | at 100 ppm = | + |
| >50% | at 33 ppm = | ++ |
| >50% | at 10 ppm = | +++ |

The results of these tests are given in Table III and IV below.

TABLE III

Larvicidal Activities of Dithioimidocarbonates

| Example Number | $R_2$ | $R_3$ | Rating |
|---|---|---|---|
| 37 | —$CH_2CH_3$ | —$CH_2S$—$CH_3$ | +++ |
| 38 | —$CH_2C\equiv CH$ | —$CH_2C\equiv CH$ | ++ |
| 39 | —$CH_2CH=CH_2$ | —$CH_2S$—$CH_3$ | +++ |
| 40 | —$CH_2CH=CH_2$ | —$(CH_2)_3CH_3$ | + |
| 41 | —$CH_2C\equiv CH$ | —$CH_2CH=CH_2$ | +++ |
| 42 | $\underset{Cl}{-CH_2\overset{|}{CH}=CH_2}$ | $\underset{Cl}{-CH_2\overset{|}{CH}=CH_2}$ | ++ |
| 43 | $-CH_2\overset{|}{C}=CH_2$ (Cl) | $-CH_2\overset{|}{C}=CH_2$ (Cl) | ++ |
| 44 | —$CH_2CH\equiv CH$ | —$CH_2CH_3$ | ++ |
| 45 | —$CH_2CH=CH_2$ | —$C(CH_3)_3$ | ++ |
| 46 | $\underset{CH_3}{-CH_2\overset{|}{C}=CH_2}$ | —$CH_2CH_3$ | +++ |
| 47 | —$CH_2$—(pyridyl) | —$CH_2CH_3$ | + |

TABLE IV

Larvicidal Activities of Dithioimidocarbonates

![structure]

| Example Number | R | $R_1$ | $R_2$ | $R_3$ | Rating |
|---|---|---|---|---|---|
| 48 | —$CH_3$ | —$CH_3$ | —$CH_2C\equiv CH$ | —$CH_2C\equiv CH$ | ++ |
| 49 | —$CH_3$ | —$CH_3$ | —$CH_2S$—$CH_3$ | —$CH_2CH=CH_2$ | +++ |
| 50 | —Cl | —Cl | $\underset{Cl}{-CH_2\overset{|}{C}=CH_2}$ | $\underset{Cl}{-CH_2\overset{|}{C}=CH_2}$ | ++ |

We claim:

1. A method of controlling ticks which comprises contacting said ticks with a fecundity-suppresing amount of a dithioimidocarbonate ester of the formula:

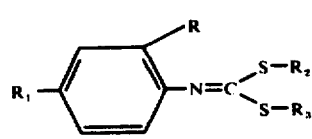

wherein R is chloro or methyl, $R_1$ is chloro or methyl, and $R_2$ and $R_3$ are each selected from the group consisting of lower alkyl, lower alkylthiomethyl, allyl, 2-chloroallyl, 2-methylallyl, propargyl, benzyl and 4-pyridylmethyl with the proviso that $R_2$ and $R_3$ cannot both be lower alkyl.

2. The method of controlling ticks according to claim 1, wherein said ticks are adult female ticks.

3. A method of controlling tick infestations on livestock, domestic pets, poultry or fur-bearing animals which comprises applying to said animals a fecundity-suppressing amount of a dithioimidocarbonate ester of the formula:

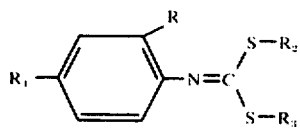

wherein R is chloro or methyl, $R_1$ is chloro or methyl, and $R_2$ and $R_3$ are each selected from the group consisting of lower alkyl, lower alkylthiomethyl, allyl, 2-chloroallyl, 2-methylallyl, propargyl, benzyl and 4-pyridylmethyl with the proviso that $R_2$ and $R_3$ cannot both be lower alkyl.

4. The method of controlling tick infestation according to claim 3, wherein said animals are livestock.

5. The method of controlling tick infestations according to claim 3, wherein said animals are domestic pets.

6. The method of controlling tick infestations according to claim 3, wherein said animals are poultry.

7. The method of controlling tick infestations according to claim 3, wherein R is methyl, $R_1$ is chloro, and $R_2$ and $R_3$ are propargyl.

8. The method of controlling tick infestations according to claim 3, wherein R is methyl, $R_1$ is chloro, $R_2$ is propargyl, and $R_3$ is ethyl.

9. The method of controlling tick infestations according to claim 3, wherein R is methyl, $R_1$ is chloro, $R_2$ is allyl, and $R_3$ is lower alkylthiomethyl.

10. The method of controlling tick infestations according to claim 3, wherein R and $R_1$ are methyl, $R_2$ is lower alkylthiomethyl, and $R_3$ is allyl.

* * * * *